United States Patent [19]

Grocela-Kathe et al.

[11] Patent Number: 5,342,430
[45] Date of Patent: Aug. 30, 1994

[54] PASSIVATION OF METHYLCHLOROSILANE FINES

[76] Inventors: Teresa A. Grocela-Kathe, 183 Pawling Ave., Troy, N.Y. 12180; Ray W. Shade, 19 El Dorado Dr., Clifton Park, N.Y. 12065

[21] Appl. No.: 98,547

[22] Filed: Jul. 28, 1993

[51] Int. Cl.$^5$ .................................................. C01G 3/00
[52] U.S. Cl. ........................................ 75/746; 75/722; 423/34; 502/29
[58] Field of Search .................. 75/746, 722; 423/34, 423/39, 140, 348; 502/556

[56] References Cited

U.S. PATENT DOCUMENTS

| | | | |
|---|---|---|---|
| 2,258,218 | 10/1941 | Rochow | 260/607 |
| 2,258,222 | 10/1941 | Rochow | 174/121 |
| 2,380,995 | 8/1945 | Rochow | 260/607 |
| 2,389,931 | 11/1945 | Reed et al. | 260/607 |
| 2,448,756 | 9/1948 | Agens | 260/37 |
| 2,449,821 | 9/1948 | Sellers et al. | 260/448.2 |
| 2,469,888 | 5/1949 | Patnode | 260/448 |
| 2,469,890 | 5/1949 | Patnode | 260/448 |
| 2,803,521 | 8/1957 | Nitzsche et al. | 423/34 |
| 4,281,149 | 7/1981 | Shade | 556/472 |
| 4,307,242 | 12/1981 | Shah et al. | 556/472 |
| 4,390,510 | 6/1983 | Ritzer et al. | 423/342 |
| 4,408,003 | 10/1983 | Robinson et al. | 524/364 |
| 4,758,352 | 7/1988 | Feidner et al. | 210/719 |
| 4,824,652 | 4/1989 | Hogokawa | 423/328 |
| 4,960,523 | 10/1990 | Degen et al. | 210/721 |
| 5,078,978 | 1/1992 | Tarbet | 75/722 |
| 5,089,049 | 2/1992 | Lischka | 75/722 |

*Primary Examiner*—Peter D. Rosenberg

[57] ABSTRACT

A process for the passivation of fine particulate matter exiting a reactor train for the manufacture of organohalosilanes comprising treating the particulate matter or fines with an aqueous medium comprising a polyalkylene ether surfactant and optionally an acidifying agent to produce hydrogen, separating the fines from the aqueous medium, and removing water from the fines.

14 Claims, No Drawings

PASSIVATION OF METHYLCHLOROSILANE FINES

FIELD OF THE INVENTION

The present invention relates to a process for deactivating, inactivating or passivating fine particulate reactive solids exiting a solids recovery portion of a reactor train wherein organohalosilanes are synthesized. The present invention also relates to means for the safe disposal or recovery of additional economically useful products from these finely divided particulate solids or fines, said fines having been passivated.

BACKGROUND OF THE INVENTION

The present invention relates to a process for treating residual silicon powder, and more particularly to a process for the passivation of residual silicon powders or fines, particularly those silicon containing powders resulting from the manufacture of halosilanes, organohalosilanes, organoalkoxysilanes, and the like. The present invention relates to the passivation, inactivation, or deactivation of the silicon fines from the fluidized bed manufacture of halo silanes, organohalosilanes, organoalkoxysilanes, and the like. The basic process for the manufacture of such silane compounds is well-known and is described in U.S. Pat. No. 2,380,995. The present invention is particularly directed to the fluidized bed process for the manufacture of halosilanes using a fluidized bed reactor similar to if not identical with the teachings as taught in U.S. Pat. No. 2,389,931. While the scope of the present invention is particularly directed to the fines generated from a fluidized bed reaction process to produce the halosilanes, organohalosilanes or organoalkoxysilanes other types of reactors used for the production of these compounds also generate fines similar in nature and composition to the fines passivated by the present invention. Some of these other reactor types involve, for example, stirred bed or fixed bed reactors in contrast to fluidized bed reactors.

Organotrichlorosilanes and diorganodichlorosilanes are two of the basic products of the above described direct process reaction. Such compounds are utilized in the production of organopolysiloxane resins as described in U.S. Pat. Nos. 2,258,218 through 2,258,222. Other products include organopolysiloxane fluids as described in U.S. Pat. Nos. 2,469,888 and 2,469,890 as well as the organopolysiloxane elastomers described in U.S. Pat. No. 2,448,756. The siloxane compounds produced by these reactions are generally used to produce linear polysiloxane fluids and polymers in the production of heat cured rubber elastomers and room temperature vulcanizable silicone rubber compositions of various types. Thus the silanes produced by the reaction process previously referenced become siloxanes and organopolysiloxane resins eventually becoming silicone rubbers and elastomers and the like.

The chemical grade silicon typical of reactor feed to the manufacturing processes referenced above has a percent silicon that is typically greater than 98% and contains to a small degree by Fe, Al, Ca, Ti and other elements making up the remainder of the composition. These trace elements are concentrated as the reaction consumes silicon to produce or manufacture the halosilanes, organohalosilanes or organoalkoxysilanes As the reaction proceeds in the fluidized bed manufacture of methylchlorosilane and other substituted silanes, small particles or fines containing silicon are ejected from the fluidized bed reactors during normal operation. Many of these particles are carried along with the crude or unpurified methylchlorosilane. The fine silicon containing particles that are captured may contain among the various constituents of the fines, reactive metals, chlorosilanes, and hydrocarbons associated with them. Prior to disposing of these fines, they must be reacted or otherwise passivated, inactivated, or deactivated before they may be safely handled and disposed. The materials must be rendered non-reactive with respect to contact with air, water or other reactive media that might be encountered by the fines.

Much of the art associated with the processing of silicon containing fines from the manufacture of organochlorosilanes has been associated with increasing the fraction of silicon reacted to form the products and increasing the efficiency of the silicon reaction in the fluidized bed reactor process. Thus there are several processes in the art for utilizing the residual silicon particles and recycling them to utilize the unreacted silicon contained therein within the process reactor train. The present process addresses the processing of these fines once they have left the silane manufacturing reactor train.

U.S. Pat. No. 4,307,242 teaches a process for recovering and recycling silicon containing fines in an organochlorosilane reactor system. The process of the '242 patent comprises a method for classifying direct process contact mass by particle size whereby the least selective, more poisoned, or impure silicon containing particles are separated from those silicon containing particles that are relatively active and selective, relatively unpoisoned, and relatively pure thereby improving the usefulness of the silicon. In the '242 patent fine effluent powder (residual contact mass or residual silicon) is directed to one or more mechanical cyclones for recovery. In the '242 patent, this fine effluent powder is generally the spent reaction mass from a reactor that produces organotrichlorosilane and diorganodichlorosilane products. According to the '242 patent, crude or impure organotrichlorosilane and diorganodichlorosilane products are recovered from the top of the cyclones and these products may contain small amounts of "very fine" entrained particles therein. The remainder of the reaction mass is treated pneumatically in the mechanical cyclones and is directed to a receiving hopper for alternate disposition. Unless the spent reaction mass is being recycled to the reactors, the '242 patent is silent on the question of alternative methods of disposing of spent reaction masses.

A method of treating spent metallic reaction masses produced in the direct process production of organohalosilanes is taught in U.S. Pat. No. 2,803,521 wherein spent, i.e. residual, silicon-containing reaction masses are dispersed in water or dilute hydrochloric acid and contacted with a chloride source at a temperature ranging from 20° to 100° C., treated with the chloride containing solution and the silicon particles allowed to settle out while the supernatant solution is treated to precipitate the dissolved metal salts and the precipitated salts are collected and re-used as fresh catalyst for the process.

Current methods involve mixing the fines with water and a binder with the object of rendering the material safe for handling. When contacted with water the fines generate hydrogen gas. Current experience is that the process is erratic, unreliable, and potentially dangerous due to the evolution of hydrogen gas. A particular problem is that the process produces lumps of unreacted fines sealed by an outer layer of reacted fines. Later rupture of these lumps exposes untreated material that may lead to a violent reaction with water. Similar problems are encountered in the briquetting operation. Thus, there are significant contacting problems associated with a simple water treatment of the fines.

SUMMARY OF THE INVENTION

Accordingly, the present invention provides a process for passivating or reacting the fines from the manufacture of organohalosilanes.

Further, the invention provides a method of reacting the fines from the manufacture of organochlorosilanes to passivate said fines such that foaming and effervescence during the process of evolving gases is controlled during the process of passivation.

The invention also provides a method of briquetting or pelletizing the fines from the manufacture of organohalosilanes once they have been passivated into a compact form suitable either as an environmentally acceptable landfill material or as raw material for further recovery and/or recovery of the metals contained in the fines.

Other advantages of the present invention will become apparent from the following description.

DETAILED DESCRIPTION OF THE INVENTION

We have discovered that using an aqueous system comprising a surfactant coupled optionally with processing said aqueous system at elevated temperatures followed subsequently by the introduction of a binder enables an improved fines passivation process wherein the fines from the halosilane manufacturing process are passivated and may be briquetted or otherwise handled for safe disposal.

An improved process for passivating fines from the manufacture of methylchlorosilane comprises introducing an effective amount of a surfactant into the aqueous reaction medium and treating the fines in the aqueous reaction medium at an elevated temperature for a sufficient time to react all the active species present that are capable of being deactivated by reaction with water, followed by introducing an effective amount of a binder and optionally briquetting the deactivated fines. While it is theorized that the three general types of surfactants, cationic, anionic, and nonionic all work to wet the surface of the fines and to improve the aqueous passivation, inactivation, or deactivation of the fines, the most preferred type of surfactant is nonionic. A more preferred surfactant is selected from the group consisting of alkyloxy(polyethyleneoxypropyleneoxy)isopropanol (commercially sold as Tergitol Min-foam 1×) and polyglycol-ether-carboxylic acid (commercially sold as Marlowet 4538). Use of cationic or anionic surfactants tends to increase the amount of foam generated when the fines are processed with the aqueous medium. When considerations regarding the amount of foaming are not critical or it is desirable to produce a somewhat less dense mass of the treated fines, then anionic or cationic surfactants could be preferred relative to nonionic surfactants.

A number of surfactants have been evaluated for their effectiveness in the aqueous passivation of the fines from the manufacture of methylchlorosilane. Polyalkylene glycol ethers and polyalkylene ether acids have been found to be the most effective surfactants. Of these materials, commercial products sold under the name of TERGITOL MIN-FOAM 1× produced and marketed by Union Carbide Corporation, alkyloxpolyetheralcohol, and MARLOWET 4538 produced and marketed by Huls, polyglycol ether carboxylic acid, are preferred. In addition to the wettability criterion usually employed to judge surfactants, the ability to minimize foaming is important since the reaction between the aqueous phase and active species contained in the fines produces hydrogen. Minimizing the amount of foam produced during the passivating process improves processability of the fines. It is also important that the any foam formed resolve, dissipate or quickly collapse because a dense cake of fines is more conveniently handled. Due to the variation in processing temperatures sometimes encountered, it is also important that the surfactant wet the fines through a wide range of temperatures. Fines passivation has been found to be a strong function of temperature, with higher temperatures increasing the rate at which hydrogen was evolved. While fines passivation may be conducted in an aqueous solution throughout the liquid range of water 0°–100° C., the higher the temperature generally the faster the process of fines passivation is completed. Therefor temperatures closer to 100° C. are more preferred, unless other considerations such as an excessive reactivity suggest a lower temperature to moderate the rate of the production of any hydrogen generated. Where it is desired to control the rate of hydrogen generation, the temperature of the aqueous medium may be controlled so that it is in the lower rnages of temperature where water exists as a liquid, such as between 0° C. and 50° C.

Not wishing to be bound by theory of presupposed mechanisms, applicants believe the surfactant assists the aqueous phase to contact all the reactive surfaces of the fines, thereby speeding up the passivation process, driving the reaction to completion, and increasing the consistency of the results obtained in the process of passivating the fines.

The point at which the binder is added to the mixture of fines and passivating agent is also important. A typical binder is calcium lignosulfonate sold commercially as NORLIG A by Lignotech. Calcium lignosulfonate has two detrimental effects. First it tends to reduce or inhibit to some extent the wetting ability of the surfactant. Second, it displays a tendency to stabilize any foam produced by the generation of hydrogen. By adding the binder after the evolution of hydrogen has ceased, these problems can be avoided and the resulting fines cake is both dense and non-dusty. A particularly important criterion for selection of the binder to be used in the briquetting operation is compatibility of the binder with respect to the chemical processes utilized to recover copper from the fines. Thus following the steps, in order of: (a) contacting said fines with an aqueous medium comprising water and a polyalkylene ether surfactant selected from the group consisting of: alkyloxy(-polyethyleneoxypropyleneoxy)isopropanol and polyglycolether-carboxylic acid; wherein the concentration of said surfactant ranges from about 0.5 to about 5.0 weight percent in said aqueous medium such that the pH of the aqueous medium is below about seven; (b) reacting said fines with said aqueous medium to produce hydrogen for a period of time ranging from about 0.25 to about 3.0 hours at a temperature ranging from about 20° C. to about 100° C. such that the additional production of hydrogen is essentially zero; (c) adding a binding agent selected from the group consisting of acid washed calcium lignosulfonate, calcium lignosulfonate, and ammonium lignosulfonate, montmorillonite, and bentonite; and (d) removing water from the mixture of fines and the aqueous medium of step (b), improves the practice in the art relative to combining all the steps simultaneously The quantities of water, surfactant, and binder necessary for practice of this invention vary due to the intrinsic variation in the reactivity of the fines. Fines reactivity appears to be related to the tapped bulk density of the fines. Both hydrogen generation and tapped bulk density appear to be correlated with reactivity. Thus, tapped bulk density may be used to set variables such as water addition and surfactant addition for proper fines treatment. It has been found that the addition of approximately one weight percent fumed silica improves the flow ability of the fines and the reproducibility of the tapped bulk density measurement. Tapped bulk density is a convenient measurement to make and easy to dispose towards use in the field.

The point in the process of passivation wherein the binder is added to the mixture of the fines and the aqueous medium containing a polyalkylene ether surfactant and an acidifying agent is also important. The purpose of adding a binding agent to the fines is to improve the physial integrity of the fines cake, i.e. to increase strength, resistance to fracture, and toreduce dusting. Certain binding agents are inappropriate to the purposes of this invention because they interfere with the desirable properties or action of the surfactant and because they may have a tendency to stabilize any foam produced by the evolution of hydrogen during treatment with the aqueous medium. Foam stabilization prevents obtaining a filter cake or compressed mass of fines in the more preferred higher densities. Examples of preferred binding agents are the smectite clays, for example, bentonite, montmorillonite, hectorite and the like. More preferred binding agents are the calcium or ammonium salts of lignosulfonic acid sold commercially by Lignotech under the trade names of Norlig A for acid washed calcium lignosulfonate, Norlig G for neutralized calcium lignosulfonate, and Lignosol AM for ammonium lignosulfonate.

One embodiment of the present invention as a method for passivating reactive silicon containing powders and yielding a final mass possessing suitable physical properties for disposal, safe transport, and economic recovery of specific components that were present in the original untreated powder comprises the following steps and considerations.

Combining the fines powder with water leading to a reaction that converts the surface of the particles from one that is chemically reactive with air and/or water to one that is chemically unreactive or passivated. When the fines are passivated, hydrogen gas is evolved from the water-fines slurry. A suitable surfactant is added to the water to enhance the dispersion of the powder in the aqueous medium and to avoid aggregation, clumping or granulation of the fines or powder particles. The use of a surfactant causes essentially all of the surface of the powder to become available to the water for reaction and thereby achieves a larger degree of passivation than would have been attainable without the use of the surfactant. Absent the surfactant, the powder tends to form clumps, intimate contact with the passivating aqueous medium is prevented and gases are entrapped. At a later time during subsequent handling or processing, these aggregates may be fractured or crushed, exposing unreacted or unpassivated surfaces and thereby leading to hazardous conditions such as fire, explosion, or both. The use of a surfactant also reduces the tendency for air-borne dust from the fine powder to be carried from the treatment site during the initial stages of mixing the fine powder into the aqueous medium. The powder is more readily wetted in the presence of the surfactant and is more quickly incorporated or dispersed into the liquid phase of the aqueous medium.

An important consideration in the selection of the surfactant is the amount of foaming that occurs during the reaction period. The degree of foaming, in turn, affects the density of the resulting final mass. The final density of the fines cake tends to a maximum when foaming during treatment with the aqueous medium is minimized. In contrast, a high degree of foaming during treatment with the aqueous medium tends to reduce the density of the resulting fines cake. Thus, depending on the relative proportions of aqueous medium and fines cake, the final mass may range from a soft pliable consistency to a dry, hard, and rigid cake depending on the residual moisture. In accordance with this discovery the degree of foaming and consequent final density of the treated fine powder may be controlled by proper selection of the surfactant to achieve the requirements of a particular end.

The rate of hydrogen evolution can be controlled by controlling the temperature of the water and the resulting slurry. By adjustment of the temperature, the evolution rate of the hydrogen can be controlled to match the handling capacity of the hydrogen handling system present. Use of very low temperatures, slows the hydrogen evolution rate to such a degree that hydrogen management may be unnecessary. When powders of different reactivities are treated the temperature may be used as a controlling factor to accommodate gas handling capacity.

The addition of a suitable binder increases the integrity and durability of the final product. The binder is preferably added following the completion of reaction between the fine powder and the aqueous medium. The presence of the binder during the reaction period has a tendency to inhibit the rate and completion of the passivation reactions. There is also the possibility that the presence of the binder during the process of reaction with the aqueous medium increases the amount of foaming and stabilizes a product with a reduced density.

The desired consistency of the final mass may be adjusted by controlling the relative amounts of powder, aqueous medium, and binder. An alternative procedure that may be employed is the use of an excess of aqueous medium to facilitate mixing. After adding the binder the water is removed by a partial or complete evaporation to achieve the desired end result.

EXAMPLES

The examples hereinafter presented serve to illustrate the utility of the new processes previously disclosed and instruct those skilled in the art concerning the broad ranges of applicability and utility wherein such new processes may be employed. By presenting these examples, applicants do not intend to imply any limitations on the extent of these new contributions to the art by the mere presentation of an illustrative example.

EXAMPLE 1

The volumes of hydrogen gas evolved as a result of aqueous treatment both with and without the addition of a nonionic surfactant were measured for a constant weight of typical fine particulates. The results are presented in tabular form as follows:

TABLE 1

USE OF SURFACTANT INCREASES HYDROGEN PRODUCED BY PASSIVATING FINES WITH AN AQUEOUS MEDIUM

| Reading Index | No Surfactant | | Surfactant = TERGITOL 1X | |
|---|---|---|---|---|
| | Time (hrs.) | Vol. H2 cc/g* | Time (hrs.) | Vol. H2 cc/g* |
| 1 | 0 | 0 | 0 | 0 |
| 2 | 0.033 | 5.00 | 0.050 | 6.55 |
| 3 | 0.117 | 10.00 | 0.083 | 11.55 |
| 4 | 0.217 | 13.60 | 0.133 | 16.55 |
| 5 | 0.283 | 15.00 | 0.233 | 21.55 |
| 6 | 0.483 | 16.75 | 0.383 | 24.35 |
| 7 | 0.683 | 17.64 | 0.500 | 25.55 |
| 8 | 0.883 | 18.25 | 0.650 | 26.55 |
| 9 | 1.030 | 18.65 | 0.817 | 27.10 |
| 10 | 1.280 | 19.00 | 1.000 | 27.75 |
| 11 | 1.450 | 19.25 | 1.267 | 28.40 |
| 12 | 2.030 | 19.90 | 3.316 | 30.35 |
| 13 | 2.920 | 19.95 | — | — |

*The volume of hydrogen generated refers to the volume generated per gram of initial charge fines on a dry weight basis. The volume is measured at 1 atmosphere and 25 +/− 5° C. The TERGITOL 1X surfactant was employed as a 2.5 weight percent solution in water.

Example 1 demonstrates that the use of a surfactant increases the amount of hydrogen evolved and also increases the rate at which it is evolved.

EXAMPLE 2

The volumes of hydrogen evolved as a function of temperature of the aqueous media being used to treat the fines.

TABLE 2

VOLUME OF HYDROGEN GENERATED INCREASES AS A FUNCTION OF INCREASING TEMPERATURE AND EVOLUTION TIME DECREASES.

| Reading Index | Temperature, °C. | Time (hr.) | Vol. H$_2$ cc/g* | Time (hr.) | Vol. H$_2$ cc/g* |
|---|---|---|---|---|---|
| | | 25 | | 90 | |
| 1 | | 0.00 | 0.20 | 0.00 | 0.00 |
| 2 | | 0.33 | 0.55 | 0.083 | 5.00 |
| 3 | | 0.92 | 0.95 | 0.200 | 10.20 |
| 4 | | 1.75 | 1.45 | 0.367 | 13.10 |
| 5 | | 2.50 | 1.90 | 0.520 | 14.10 |
| 6 | | 2.75 | 2.05 | 0.716 | 15.20 |
| 7 | | 4.08 | 2.70 | 1.050 | 16.05 |
| 8 | | 5.00 | 3.10 | 1.320 | 16.60 |
| 9 | | 5.50 | 3.30 | 1.870 | 17.25 |
| 10 | | 6.00 | 3.50 | 3.830 | 18.10 |
| 11 | | 6.67 | 3.80 | | |
| 12 | | 7.42 | 4.05 | | |
| 13 | | 7.92 | 4.20 | | |

*The volume of hydrogen generated refers to the volume generated per gram of initial charge fines on a dry weight basis. The volume is measured at 1 atmosphere and 25 +/− 5° C.

Example 2 demonstrates that an increase in temperature increases the amount of hydrogen produced during the passivation or deactivation process; the example also demonstrates that the time required to achieve a state of low hydrogen generation activity is also decreased. This example demonstrates that the hydrogen generation rate may be controlled by controlling the temperature of the passivation process.

EXAMPLE 3

This example illustrates the wide variation in the activity of the fine particulate matter being passivated by the processes of applicants' invention.

TABLE 3

| Reading Index | Sample Date | Time (hr.) | Vol. H$_2$ cc/g* | Time (hr.) | Vol. H$_2$ cc/g* | Time (hr.) | Vol. H$_2$ cc/g* | Time (hr.) | Vol. H$_2$ cc/g* |
|---|---|---|---|---|---|---|---|---|---|
| | | 7/2/92 | | 8/24/92 | | 8/26/92 | | 8/28/92 | |
| 1 | | 0.00 | 0.00 | 0.00 | 0.00 | 0.00 | 0.00 | 0.00 | 0.00 |
| 2 | | 0.05 | 6.55 | 0.017 | 5.00 | 0.033 | 5.00 | 0.05 | 2.50 |
| 3 | | 0.083 | 11.55 | 0.033 | 10.00 | 0.05 | 10.00 | 0.10 | 5.00 |
| 4 | | 0.133 | 16.55 | 0.050 | 15.00 | 0.067 | 15.00 | 0.18 | 7.10 |
| 5 | | 0.233 | 21.55 | 0.067 | 20.00 | 0.083 | 20.00 | 0.35 | 8.60 |
| 6 | | 0.383 | 24.35 | 0.083 | 25.00 | 0.092 | 25.00 | 0.55 | 10.10 |
| 7 | | 0.500 | 25.55 | 0.100 | 30.00 | 0.100 | 30.00 | 1.32 | 11.20 |
| 8 | | 0.650 | 26.55 | 0.117 | 35.00 | 0.117 | 35.00 | 1.85 | 11.50 |
| 9 | | 0.817 | 27.10 | 0.150 | 40.00 | 0.150 | 40.00 | | |
| 10 | | 1.000 | 27.75 | 0.217 | 45.00 | 0.217 | 45.00 | | |
| 11 | | 1.267 | 28.40 | 0.300 | 48.20 | 0.35 | 48.50 | | |
| 12 | | 3.316 | 30.35 | 0.383 | 50.10 | 0.43 | 50.00 | | |
| 13 | | | | 0.533 | 52.10 | 0.517 | 50.90 | | |
| 14 | | | | 0.700 | 53.50 | 0.683 | 52.10 | | |
| 15 | | | | 0.967 | 54.70 | 0.850 | 52.75 | | |
| 16 | | | | 1.583 | 56.20 | 1.067 | 53.45 | | |
| 17 | | | | 3.450 | 56.40 | 1.800 | 54.65 | | |

*The volume of hydrogen generated refers to the volume generated per gram of initial charge fines on a dry weight basis. The volume is measured at 1 atmosphere and 25 +/− 5° C.

Example three demonstrates that the activity of the fines to be passivated, deactivated or inactivated by applicants' invention may vary by a factor of at least five.

EXAMPLE 4

This example demonstrates that the generation of hydrogen from fines at constant experimental conditions is related to the surface area of the fines as measured by a single point BET surface area.

TABLE 4

HYDROGEN GENERATION BY FINES IS RELATED TO BET SURFACE AREA.

| Reading Index | Hydrogen Generation cc/g* | Surface Area $m^2/g$ |
|---|---|---|
| 1 | 56.40 | 9.08 |
| 2 | 54.70 | 8.30 |
| 3 | 30.35 | 5.03 |

*The volume of hydrogen generated refers to the volume generated per gram of initial charge fines on a dry weight basis. The volume is measured at 1 atmosphere and 25 +/− 5° C.

Example 4 demonstrates a relationship between the surface area of the fines as measured by a single point BET surface area and the quantity of hydrogen generated at constant conditions.

EXAMPLE 5

This example demonstrates a relationship between the bulk density of fines and the hydrogen generated during the process of passivating, inactivating, or deactivating the fines using an aqueous medium.

TABLE 5

BULK DENSITY IS RELATED TO HYDROGEN GENERATION AND SURFACE AREA

| Reading Index | Hydrogen Generation cc/g* | Surface Area $m^2/g$ | Bulk Density g/cc** |
|---|---|---|---|
| 1 | 56.40 | 9.08 | 0.9646 |
| 2 | 54.70 | 8.30 | 1.0350 |
| 3 | 30.35 | 5.03 | 1.2630 |
| 4 | 11.50 | N/A | 1.4400 |

*The volume of hydrogen generated refers to the volume generated per gram of initial charge fines on a dry weight basis. The volume is measured at 1 atmosphere and 25+/−5° C.
**The bulk density was measured by adding 1 weight percent of finely divided silica to the fines and then measuring bulk density of the fines silica mixture. The addition of the silica to the fines improves the reliability of the bulk density measurement by eliminating clumping or bridging of the fines thereby permitting ready escape of entrapped gas.

Example five demonstrates the interrelationship between bulk density, surface area, and the volume of hydrogen generated during treatment with the aqueous medium.

EXAMPLE 6

The following example demonstrates the approximate equivalence of hydrogen ion concentrations at pH's lower than about 7 and the non-equivalence of basic solutions at pH's greater than about 8 for the aqueous treating media utilized to passivate, deactivate, or inactivate the fines.

TABLE 6

EFFECT OF HYDROGEN ION CONCENTRATION ON THE GENERATION OF HYDROGEN FROM HALOSILANE MANUFACTURING FINES.

| Reading | pH | Time (hr.) | Vol. $H_2$ cc/g* 4 | Time (hr.) | Vol. $H_2$ cc/g* 6 | Time (hr.) | Vol. $H_2$ cc/g* 8 |
|---|---|---|---|---|---|---|---|
| 1 | 0.00 | 0.00 | 0.00 | 0.00 | 0.00 | 0.00 | 0.00 |
| 2 | 0.033 | 5.40 | 0.050 | 6.55 | 0.033 | 5.00 | |
| 3 | 0.150 | 10.40 | 0.083 | 11.55 | 0.050 | 10.00 | |
| 4 | 0.200 | 15.40 | 0.133 | 16.55 | 0.067 | 15.00 | |
| 5 | 0.283 | 20.40 | 0.233 | 21.55 | 0.083 | 20.00 | |
| 6 | 0.400 | 23.15 | 0.383 | 24.35 | 0.100 | 25.00 | |
| 7 | 0.700 | 25.40 | 0.500 | 25.55 | 0.133 | 30.00 | |
| 8 | 0.817 | 25.85 | 0.650 | 26.55 | 0.183 | 35.00 | |
| 9 | 0.983 | 26.40 | 0.817 | 27.10 | 0.250 | 40.00 | |
| 10 | 1.150 | 26.95 | 1.000 | 27.75 | 0.383 | 45.00 | |
| 11 | 1.400 | 27.25 | 1.267 | 28.40 | 0.517 | 47.20 | |

TABLE 6-continued

EFFECT OF HYDROGEN ION CONCENTRATION ON THE GENERATION OF HYDROGEN FROM HALOSILANE MANUFACTURING FINES.

| Reading | pH | Time (hr.) | Vol. $H_2$ cc/g* 4 | Time (hr.) | Vol. $H_2$ cc/g* 6 | Time (hr.) | Vol. $H_2$ cc/g* 8 |
|---|---|---|---|---|---|---|---|
| 12 | 1.650 | 27.60 | 3.316 | 30.35 | NM | NM | |
| 13 | 2.030 | 28.05 | | | 0.800 | 49.50 | |
| 14 | 2.550 | 28.05 | | | 1.150 | 51.15 | |
| 15 | | | | | 1.670 | 51.45 | |

*The volume of hydrogen generated refers to the volume generated per gram of initial charge fines on a dry weight basis. The volume is measured at 1 atmosphere and 25 +/− 5° C.

Example six demonstrates that there are small differences in the quantity of hydrogen evolved below pH levels of about 7 but under basic conditions beginning at about pH 8 considerably more hydrogen is evolved per unit weight of the fines. While not wishing to be bound by theory, applicants suggest that the basic conditions of pH levels greater than about 8 are leading to a basic hydrolysis of the silicon present in the fines thereby producing hydrogen. In practice it is usually not beneficial to solubilize the silicon present in the fines, thus pH levels lower than about 7 are preferred.

When it is desirable or necessary to adjust the hydrogen ion concentration of the aqueous treating medium, the acids that may be used to adjust the hydrogen ion concentration of the aqueous treating medium may be any one of several mineral acids selected from the group consisting of sulfuric, phosphoric, and the hydrohalic acids with the exception of hydrofluoric. Nitric acid, while it may also be used since it is a mineral acid, does present the problem of oxidation of any oxidizable metals present, for example copper. Suitable organic acids such as formic and acetic acids may also be employed to adjust the hydrogen ion content of the aqueous treating medium. For those acids that are dibasic or tribasic such as sulfuric and phosphoric acids or dibasic organic acids, environmentally acceptable acid salts may also be utilized to adjust the hydrogen ion concentration. Such environmentally acceptable salts would be those partially neutralized by the alkali metals, ammonia, and various low molecular weight organic amines.

EXAMPLE 7

An aqueous mixture, solution, or slurry containing approximately 58 weight percent acid washed calcium lignosulfonate, binder, commercially sold under the trade name of Norlig A by Lignotech was mixed with dry fines at a weight ratio of 1 gm of aqueous mixture, solution, or slurry to 7 gm of fines. The mixture comprising the fines, the binder, and the aqueous medium formed a slurry. The slurry was poured into a container and dried in an oven at a temperature of about 150° C. After removing the water from the slurry by drying, the fines and the binder formed a compact mass similar to a briquette. In this example the solid cake or briquette-like material had a binder content of about 8 weight percent.

EXAMPLE 8

Example 7 was repeated at a higher level of binder. In example 8, the weight of the aqueous mixture, solution or slurry was increased to 11 gm per 50 gm of weight of the fines. In this example the fines cake or casting, approximating a product briquette, had a binder content of 12.7 weight percent.

Applicants believe that the operative ranges for best performance to be attained using a lignosulfonate type binder are from about 5 to about 20 weight percent when it is desired to manufacture a briquette. When it is desired to manufacture a low dusting level granular form of the fines cake, the level of binder may be dropped to a range of from about 1 to about 5 weight percent.

Having described the invention that which is claimed is:

1. A process for passivating the fines exiting the reactor train for the manufacture of organohalosilanes and alkoxyhalosilanes comprising the steps, in order of:
   (a) contacting said fines with an aqueous medium comprising water and a polyalkylene ether surfactant selected from the group consisting of: alkyloxy(polyethyleneoxypropyleneoxy)isopropanol and polyglycolether-carboxylic acid; wherein the concentration of said surfactant ranges from about 0.5 to about 5.0 weight percent in said aqueous medium such that the pH of the aqueous medium is below about seven;
   (b) reacting said fines with said aqueous medium to produce hydrogen for a period of time ranging from about 0.25 to about 3.0 hours at a temperature ranging from about 20° C. to about 100° C. such that the additional production of hydrogen is essentially zero;
   (c) adding a binding agent selected from the group consisting of acid washed calcium lignosulfonate, calcium lignosulfonate, ammonium lignosulfonate, montmorillonite, and bentonite; and
   (d) removing water from the mixture of fines, binder, and the aqueous medium of step (c).

2. The process of claim 1 where the surfactant is alkyloxy(polyethyleneoxypropyleneoxy)isopropanol.

3. The process of claim 1 where the temperature ranges from about 80° C. to about 100° C.

4. The process of claim 3 where the surfactant is alkyloxy(polyethyleneoxypropyleneoxy)isopropanol.

5. The process of claim 1 where the temperature ranges from about 90° C. to about 100° C.

6. The process of claim 5. where the surfactant is alkyloxy(polyethyleneoxypropyleneoxy)isopropanol.

7. The process of claim 1 where the surfactant is polyglycol-ether-carboxylic acid.

8. The process of claim 7 where the temperature ranges from about 80° C. to about 100° C.

9. The process of claim 8 where the surfactant is polyglycol-ether-carboxylic acid.

10. The process of claim 9 where the temperature ranges from about 90° C. to about 100° C.

11. The process of claim 1 where the temperature ranges from about 20° to about 80° C.

12. The process of claim 1 wherein the temperature of the aqueous medium ranges from about 0° C. to about 80° C.

13. The process of claim 1 wherein the temperature of the aqueous medium ranges from about 0° C. to about 50° C.

14. The process of claim 1 wherein the temperature of the aqueous medium ranges from about 25° C. to about 50° C.

* * * * *